United States Patent
Whitlow et al.

(10) Patent No.: US 9,037,523 B2
(45) Date of Patent: May 19, 2015

(54) MULTIPLE TWO-STATE CLASSIFIER OUTPUT FUSION SYSTEM AND METHOD

(75) Inventors: Stephen Whitlow, St. Louis Park, MN (US); Michael Christian Dorneich, Saint Paul, MN (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 981 days.

(21) Appl. No.: 13/082,135

(22) Filed: Apr. 7, 2011

(65) Prior Publication Data

US 2012/0259803 A1    Oct. 11, 2012

(51) Int. Cl.
*G06E 1/00* (2006.01)
*A61B 5/00* (2006.01)
*A61B 5/16* (2006.01)

(52) U.S. Cl.
CPC .......... *A61B 5/4884* (2013.01); *A61B 5/16* (2013.01); *A61B 5/7264* (2013.01); *A61B 2503/12* (2013.01)

(58) Field of Classification Search
USPC .......................................................... 706/20
See application file for complete search history.

(56) References Cited

U.S. PATENT DOCUMENTS

| | | | |
|---|---|---|---|
| 5,552,169 A | 9/1996 | Kannankeril et al. | |
| 5,815,070 A | 9/1998 | Yoshikawa | |
| 7,039,551 B2 | 5/2006 | Shu et al. | |
| 7,054,723 B2 | 5/2006 | Seto et al. | |
| 7,088,264 B2 * | 8/2006 | Riley | 340/963 |
| 7,292,152 B2 * | 11/2007 | Torkkola et al. | 340/576 |
| 7,565,230 B2 | 7/2009 | Gardner et al. | |
| 7,830,249 B2 | 11/2010 | Dorneich et al. | |
| 2001/0016855 A1 * | 8/2001 | Hiroshige | 707/503 |
| 2008/0281170 A1 * | 11/2008 | Eshelman et al. | 600/301 |
| 2008/0300534 A1 | 12/2008 | Blomquist | |
| 2009/0082637 A1 | 3/2009 | Galperin | |
| 2010/0057277 A1 * | 3/2010 | Goodrich et al. | 701/14 |
| 2010/0069775 A1 | 3/2010 | Milgramm et al. | |
| 2010/0100001 A1 | 4/2010 | Aguilar et al. | |
| 2010/0182139 A1 | 7/2010 | Chen et al. | |
| 2010/0185113 A1 * | 7/2010 | Peot et al. | 600/544 |
| 2010/0217097 A1 * | 8/2010 | Chen et al. | 600/301 |
| 2010/0241021 A1 | 9/2010 | Morikawa et al. | |

FOREIGN PATENT DOCUMENTS

| | | |
|---|---|---|
| JP | 05-316993 | 12/1993 |
| JP | 2001-294677 | 10/2001 |
| WO | 2010-114879 | 10/2010 |

OTHER PUBLICATIONS

European Patent Office, European Office Action dated Nov. 5, 2012.
Wilson, et al.; Operator Functional State Classification Using Multiple Psychophysiological Features in an Air Traffic Control Task, Human Factors, vol. 45, No. 3, Fall 2003, pp. 381-389.
Extended EP Search Report for 12 162 867.1 dated Aug. 14, 2012.
EP Examination Report for Application No. 12162867.1 dated Aug. 26, 2014.

* cited by examiner

*Primary Examiner* — Kakali Chaki
*Assistant Examiner* — Mai T Tran
(74) *Attorney, Agent, or Firm* — Ingrassia Fisher & Lorenz, P.C.

(57) ABSTRACT

A system and method for providing more than two levels of classification distinction of a user state are provided. The first and second general states of a user are sensed. The first general state is classified as either a first state or a second state, and the second general state is classified as either a third state or a fourth state. The user state of the user is then classified as one of at least three different classification states.

13 Claims, 3 Drawing Sheets

MULTIPLE TWO-STATE CLASSIFIER OUTPUT FUSION SYSTEM AND METHOD

TECHNICAL FIELD

The present invention generally relates to user state classification, and more particularly relates to systems and methods for fusing the outputs of multiple two-state classifiers to achieve increased state level discrimination.

BACKGROUND

Modern complex systems can place both high and low levels of cognitive demands on human operators. If operators do not maintain an optimal cognitive state, then overall system performance may suffer. For example, if an operator is in a relatively high cognitive state, the likelihood that the operator may make an error increases and system performance may degrade. As a result, when the suitability of new or modified systems is tested, accurate assessment of operator functional state is required. If the system places demands on the operator beyond his or her capabilities, then the system or operational procedures must be modified. On the other hand, high levels of automation can lead to complacency, which may result in the operator losing awareness of the system's true state. This situation can also lead to reduced performance and increased errors. In some circumstances it may be possible for the system to adapt the task to meet the momentary needs of the operator. For example, if the operator is becoming mentally overloaded, the system may be able to automate some aspects of the task to reduce the cognitive demands on the operator. The reduced task demands should lead to reduced operator mental workload and enhanced performance. Accurate estimations of operator functional state are thus desirable in these situations.

From the foregoing, it may be appreciated that operator state classification is becoming increasingly used across multiple domains. However, current operator state classification systems classify a general operator state, such as workload state, into one of two classification states—high workload state and low workload state. This is because known two-state classifiers generally provide relatively robust classification performance. While it is generally desired to classify greater than two states of a given dimension, various research has demonstrated a decrement when attempting to do. For example, one set of researchers documented that discriminating four levels of workload state yielded classification performance between 84-88%, whereas two levels, using the same data, yielded classification performance of about 98%.

One of the goals of next generation adaptive systems is the capability to implement more precise adaptations. It is believed that this goal may be realized if three, four, or even more levels of a user states can be distinguished. For example, as was noted above, current classification systems may classify operator workload state as either a low workload state or a high workload state. This is not only because these two states are distinct and have operational relevance, but because they are relatively easy to distinguish. However, there may be some instances where knowing that an operator is experiencing nominal workload, compared to low or high workload, could provide higher resolution state tracking and adaptation selection. However, to insure user acceptance and trust, classification performance above 90% will likely be needed.

Hence, there is a need for a system and method that provides increased state level discrimination, as compared to presently known multi-level classifiers. The present invention addresses at least this need.

BRIEF SUMMARY

In one embodiment, a system for providing more than two levels of classification distinction of a user state includes a first two-state classifier, a second two-state classifier, and a classifier fusion module. The first two-state classifier is configured to receive data representative of a first general state of a user and, upon receipt thereof, to classify the first general state of the user as either a first state or a second state and supply a first classification output representative thereof. The second two-state classifier is configured to receive data representative of a second general state of the user and, upon receipt thereof, to classify the second general state of the user as either a third state or a fourth state and supply a second classification output representative thereof. The classifier fusion module is coupled to receive the first classification output and the second classification output and is configured, upon receipt thereof, to classify the user state as one of at least three different classification states.

In another embodiment, a method for classifying a user state includes sensing a first general state of a user and sensing a second general state of a user. A first two-state classifier is used to classifying the first general state of the user as either a first state or a second state to determine a first user classification. A second two-state classifier is used to classify the second general state of the user as either a third state or a fourth state to determine a second user classification. The user state is classified as one of at least three different classification states based on the first user classification and the second user classification.

Furthermore, other desirable features and characteristics of the disclosed system and method will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
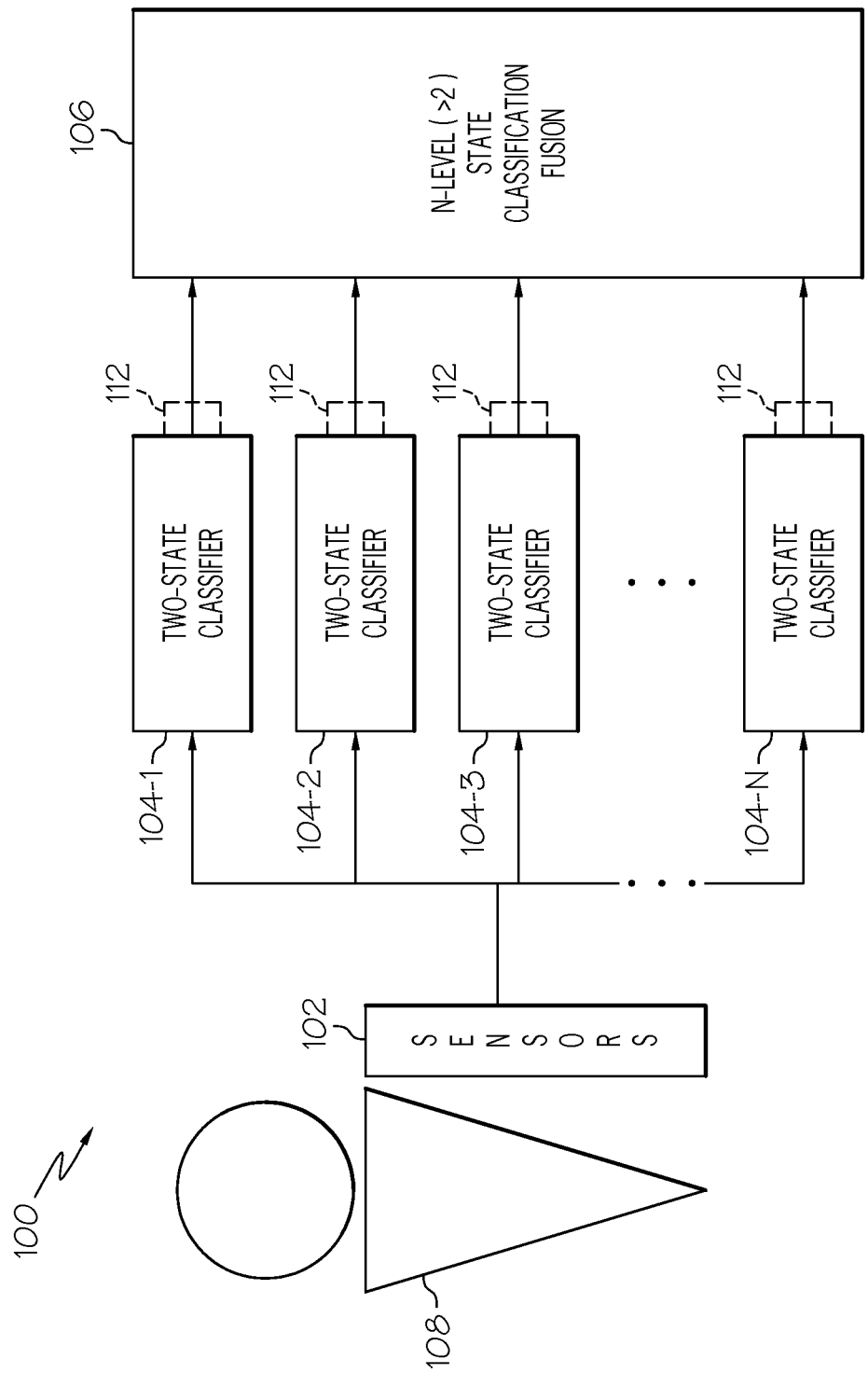
FIG. 1 depicts a functional block diagram of one exemplary embodiment of a two-state classifier output fusion system.

Referring to FIG. 1, a functional block diagram of one exemplary embodiment of a two-state classifier output fusion system 100 is depicted. The depicted system 100 includes a plurality of sensors 102 (102-1, 102-2, 102-3, ... 102-N), a plurality of two-state classifiers 104 (104-1, 104-2, 104-3, ... 104-N), and a classifier fusion module 106. Before describing each of these portions of the depicted system 100 in more detail, it is noted that although the two-state classifiers 104 and the classifier fusion module 106 are each depicted as separate functional blocks, this is done merely for clarity and ease of illustration and description. In some embodiments, some or all of the two-state classifiers 104 could be implemented as part of a single processing circuit. Moreover, the classifier fusion module 106 could also be implemented as part of the same processing circuit as one or more of the two-state classifiers 104.

Returning again to the system description, the sensors 102 are each configured to sense and supply data representative of a general state of a user 108 to one or more of the two-state classifiers 104. The particular type of sensor data may vary depending, for example, on the particular general user state (or states) of interest. Some non-limiting examples of sensor data include physiological data, contextual data, and/or various other relevant data. The sensors 102 may be located on the body and/or clothing of a user 108, and/or on one or more other devices (e.g., helmet, eye wear) worn by the user 108. In some implementations, one or more of the sensors 102 may be disposed nearby the user 108.

It will additionally be appreciated that the number and type of sensors 102 may vary. Some non-limiting examples of suitable physiological sensors include an electroencephalogram (EEG) sensor, an electrocardiogram (ECG) sensor, an electro-oculogram (EOG) sensor, an impedance pneumogram (ZPG) sensor, a galvanic skin response (GSR) sensor, a blood volume pulse (BVP) sensor, a respiration sensor, an electromyogram (EMG) sensor, a pupilometry sensor, a visual scanning sensor, a blood oxygenation sensor, a blood pressure sensor, a skin and core body temperature sensor, a near-infrared optical brain imaging sensor, or any other device that can sense physiological changes in the user.

The EEG sensors monitor the user's brain wave activity by sensing electrical potentials at the scalp. Measurements by the EEG sensors are categorized into frequency bands, including delta, theta, alpha, and beta. For example, the delta band ranging from 1-4 Hz indicates a state of unconsciousness, the theta band ranging from 4-8 Hz indicates a state of daydreaming, the alpha band ranging from 8-13 Hz indicates an alert, but not mentally busy state, and the beta band ranging from 13-30 Hz indicates a state of higher thought process. Other frequency bands are possible. Based on the location of the EEG sensors, and the dominant frequencies detected, EEG data may help evaluate the type and amount of mental activity of the user 108. For example, if there are significant brain waves measured in the frontal areas of the brain, the user 108 may be actively manipulating information within their working memory. As a result, the EEG sensors may be used to measure the cognitive state of the user 108.

Other physiological sensors mentioned above include ECG sensors, EOG sensors, ZPG sensors, GSR sensors, pupilometry sensors, visual scanning sensors, blood oxygenation sensors, BVP sensors, EMG sensors, blood pressure sensors, and near-infrared optical brain imaging sensors. The ECG sensors measure heart rate by detecting electrical activity of the heart muscle. The EOG sensors measure eye movement by detecting electrical changes between the front and back of the eye as the eye moves. The ZPG sensors (or other type of respiration sensors) measure lung capacity and can be used to determine whether the user 108 is having difficulty breathing. The GSR sensors measure changes in conductivity of the skin caused by sweating and saturation of skin ducts prior to sweating. The pupilometry sensors measure pupil dilation to determine the level of engagement or interest in a task, or cognitive load of a task. The visual scanning sensors measure scanning behavior and dwell time to provide insight into visual attention. The blood oxygenation sensors sense oxygen levels in the blood. The BVP sensors measure heart rate by detecting changes in blood volume at a given location of the body. The EMG sensors measure currents associated with muscle action. The near-infrared optical brain imaging sensors measure brain function.

The sensors 102 may additionally include an accelerometer, an acoustic sensor, an eye tracker, or any other device that can sense contextual data. These sensor types may be commercial off-the-shelf devices or custom designed. The accelerometers, if included, measure the rate at which an object is moving, the acoustic sensors, if included, measure the loudness and frequency of ambient sounds, and the eye trackers, if included, measure pupilometry and/or visual scanning behavior. Data from the accelerometers may be used to measure head movement such as yaw, pitch, and roll. Data from the eye trackers may be used to infer cognitive state from pupil dilation response and to infer visual attention indices from dwell time and scanning patterns.

No matter the specific number and type of sensors 102 used, each sensor 102 supplies data representative of the measured stimuli to one or more of the two-state classifiers 104. It will be appreciated that the data may be transmitted to the two-state classifiers 104 wirelessly or via hard-wired connections, and that the data may be modified, prior to transmission, to format the data as needed.

The two-state classifiers 104 are each coupled to receive sensor data from one or more of the sensors 102 and, upon receipt of the sensor data, to classify a different general user state of the user 108 as being one of two different states (e.g., a first state or a second state). Each two-state classifier 104 is additionally configured to supply a classification output representative of the general user state. For example, the first two-state classifier 102-1 is coupled to receive data representative of a first general state of the user 108 and is configured, upon receipt of the data, to classify the first general user state as either a first state or a second state and supply a first classification output representative thereof, the second two-state classifier 102-2 is coupled to receive data representative of a second general state of the user 108 and is configured, upon receipt of the data, to classify the second general state of the user as either a third state or a fourth state and supply a second classification output representative thereof, and so on.

As is generally known, a classifier is an algorithm, or collection of algorithms, that can be used to classify user states. More specifically, a classifier implements an individualized discriminant function, generated by a machine learning algorithm that has been trained on data sets. For two-state classifiers 104, such as those implemented in the depicted system 100, the two different states are established a priori. There are two general categories of classifiers that may be used to classify user states. These two categories are linear classifiers and nonlinear classifiers. Linear classifiers include classification algorithms that are generated via logistic regression analysis or linear discriminant analysis. Nonlinear classifiers include artificial neural networks (ANNs) and support vector machines. The two-state classifiers 104 in the system of FIG. 1 may be implemented using any one of numerous linear classifiers or any one of numerous nonlinear classifiers, as needed or desired. In some embodiments, the output of the two-state classifiers 104 can be jittery, and each can also exhibit undesirable temporal response resolution. Thus, as FIG. 1 further depicts in phantom, a median filter 112 may be applied to the output of each of the two-state classifiers 104.

It will additionally be appreciated that the number and specific type of general user states that each classifier 104 is configured to classify may vary. For example, in some embodiments, the general user states may include user workload state, user cognitive state, user alertness state, working memory load, visual attention activity, global state indicative of expert performance, continuous performance measure, and physiological arousal state, just to name a few. If a classifier 104 is configured to classify user workload state, it may classify the user 108 as being in a high workload state or a low workload state. If a classifier 104 is configured to classify user working memory state, it may classify the user 108 as being in a high working memory state or a low working memory state. If a classifier 104 is configured to classify user alertness state, it may classify the user 108 as being in a high drowsiness state or a low drowsiness state.

No matter the specific number and type of two-state classifiers 104 that are used, each classifier 104 supplies its classification output to the classifier fusion module 106. The classifier fusion module 106 is configured, upon receipt of each classification output, to classify the state of the user 108 as being one of greater than two different classification states. It will be appreciated that the number of different classification states may vary depending, for example, on the number of different two-state classifiers 104 that are used. For example, if 2 two-state classifiers 104 are used, the classifier fusion module 106 may be configured to classify the state of the user 108 as being one of three or four different classification states. If 3 two-state classifiers 104 are used, the classifier fusion module 106 may be configured to classify the state of the user 108 as being one of three, or four, or five, etc., up to eight different classification states. If N-number two-state classifiers 104 are used, the classifier fusion module 106 may be configured to classify the state of the user 108 as being one of three, or four, or five, etc., up to $2^N$ different classification states.

Figure 2:
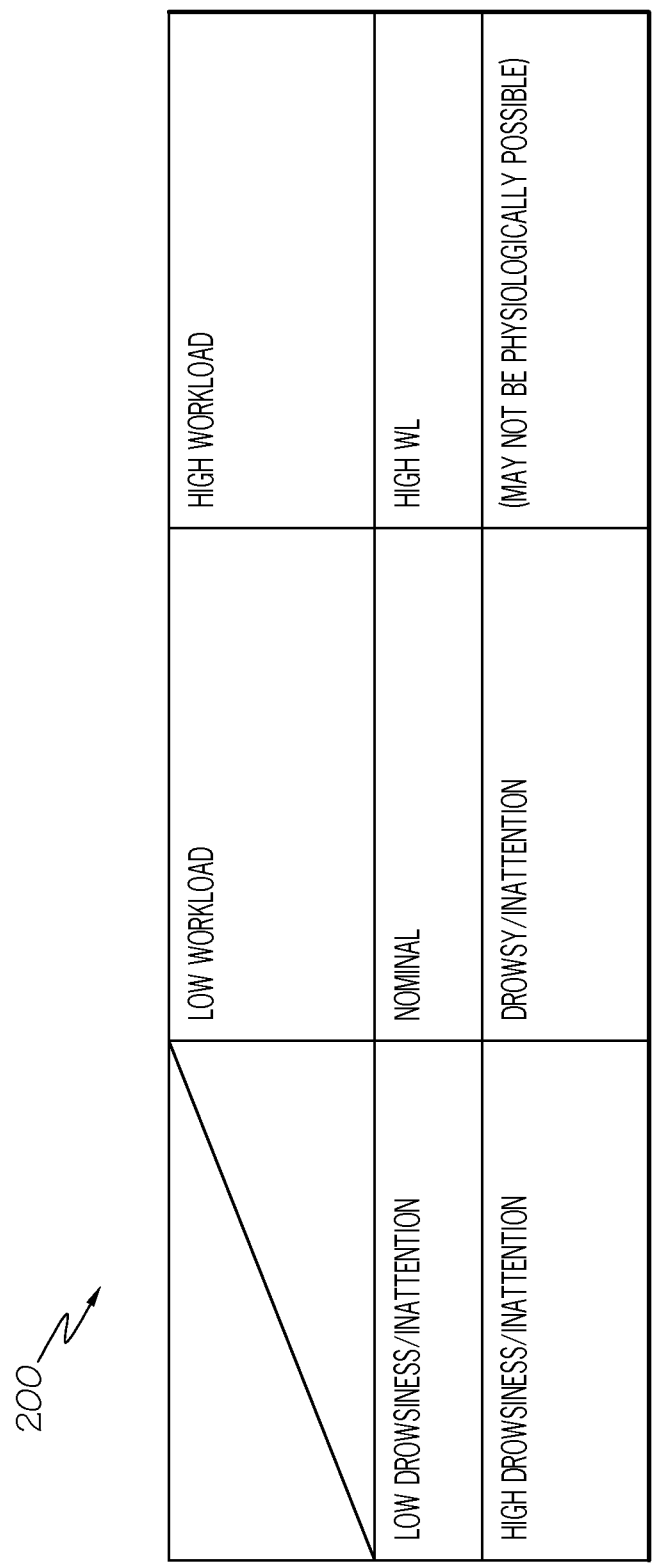
FIG. 2 depicts an example, in tabular form, of how the outputs of two different two-state classifiers may be fused into a suitable combinational construct.

As may be appreciated, the different user states that the classifier fusion module 106 classifies are preferably relevant to the end-use environment of the system 100 and sufficiently related to fuse into a meaningful combinational construct, so that the fused output is sensible and understandable. For example, if the system 100 is implemented in an aircraft, user (e.g., pilot) workload state and pilot drowsiness/inattention state can by highly relevant to aircraft operations, and are also sufficiently related. One example of a suitable combinational construct is depicted in tabular form in FIG. 2. The depicted table 200 illustrates one example of how the output of two different two-state classifiers 104—a workload state classifier and a drowsiness/inattention state classifier—may be fused to provide either 3 or 4 different classification states. It is noted that the depicted construct 200 may provide only 3 different classification states since, as indicated, it may not be physiologically possible for a user 108 to be both in both a high drowsy/inattentive state and in a high workload state.

Figure 3:
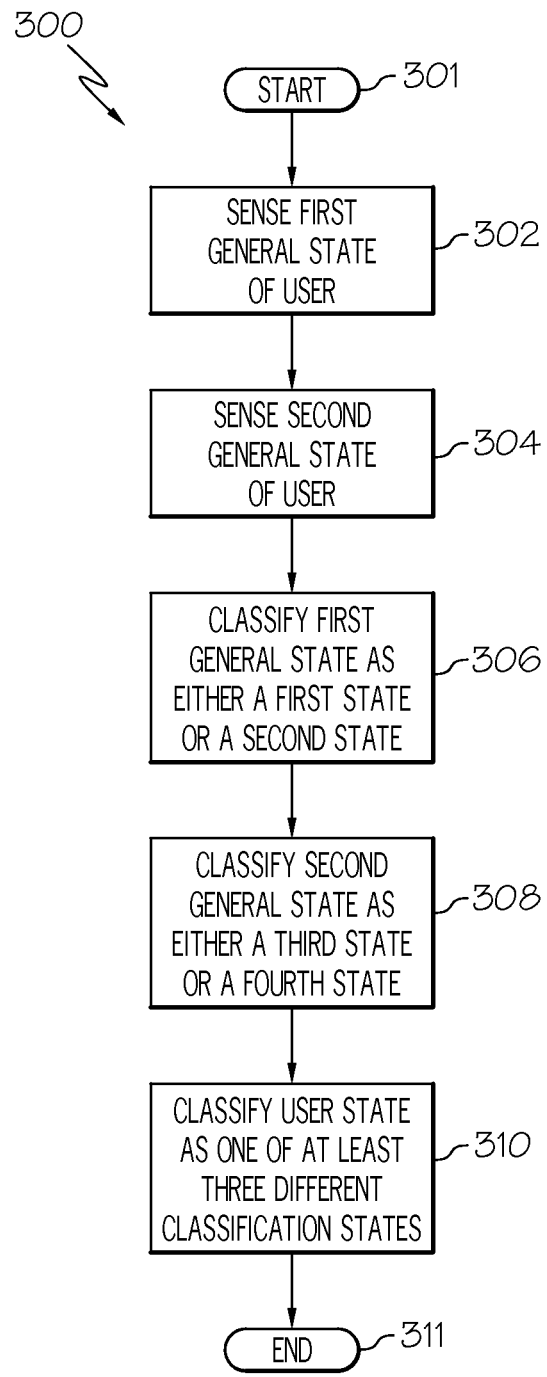
FIG. 3 depicts a process, in flowchart form, that may be implemented by the system of FIG. 1.

The general methodology that is implemented by the two-state classifier output fusion system 100, and that was described above, is depicted in flowchart form in FIG. 3. For completeness, a description of this method 300 will now be provided. In doing so, it is noted that the parenthetical references refer to like-numbered flowchart blocks. It is additionally noted that the depicted method 300 may be implemented in a system 100 that is includes only 2 two-state classifiers 104, a first two-state classifier 104-1 that is used to classify a first general user state and a second two-state classifier 104-2 that is used to classify a second general user state. The skilled artisan will readily understand how to expand the depicted methodology for a system with three or more two-state classifiers 104.

With the above background in mind, the depicted method 300 begins by sensing the first general state of the user 108 (302) and the second general state of the user 108 (304). The first general state is classified as either a first state or a second state (306), and the second general state is classified as either a third state or a fourth state (308). The user state is then classified as one of at least three different classification states (310).

Depending upon the end-use environment in which the system 100 is implemented, the output of classifier fusion module 106 may be used to generate various types of alerts and/or cause one or more displays or other devices to be reconfigured and/or configure one or more other systems to switch from a manual mode to an automatic mode or vice-versa. These are merely some non-limiting examples of the various resultants that can be provided by the system 100.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The word "exemplary" is used exclusively herein to mean "serving as an example, instance, or illustration." Any embodiment described herein as "exemplary" is not necessarily to be construed as preferred or advantageous over other embodiments.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A system for providing more than two levels of classification distinction of a user state, comprising:
   a first two-state classifier implemented in hardware, the first two-state classifier configured to receive data representative of a first general state of a user and, upon receipt thereof, to classify the first general state of the user as either a first state or a second state and supply a first classification output representative thereof;
   a second two-state classifier implemented in hardware, the second two-state classifier configured to receive data representative of a second general state of the user and, upon receipt thereof, to classify the second general state of the user as either a third state or a fourth state and supply a second classification output representative thereof; and
   a classifier fusion module implemented in hardware, the classifier fusion module coupled to receive the first classification output and the second classification output and configured, upon receipt thereof, to classify the user state as one of at least three different classification states using a predetermined multi-dimensional combinational construct.

2. The system of claim 1, wherein the predetermined combinational construct comprises a multi-dimensional table.

3. The system of claim 1, wherein the first general state and the second general state are functionally related.

4. The system of claim 1, further comprising:
   a third two-state classifier implemented in hardware, the third two-state classifier configured to receive data representative of a third general state of the user and, upon receipt thereof, to classify the third general state of the user as either a fifth state or a sixth state and supply a third classification output representative thereof to the classifier fusion module,
   wherein the classifier fusion module is further configured, upon receipt of the third classification output, to classify the user state as one of up to eight different classification states.

5. The system of claim 1, further comprising:
   (N−2) additional two-state classifiers implemented in hardware, each additional two-state classifier configured to receive data representative of a different general state of the user and, upon receipt thereof, to classify the different general state of the user as one of two states and supply a different additional classification output representative thereof to the classifier fusion module,
   wherein the classifier fusion module is further configured, upon receipt of each of the additional different classification outputs, to classify the user state as one of up to $2^N$ different classification states.

6. A system for providing more than two levels of classification distinction of a user state, comprising:
   N-number of two-state classifiers implemented in hardware, each two-state classifier configured to receive data representative of a different general state of a user and, upon receipt thereof, to classify the different general state of the user as one of two states and supply a different classification output representative thereof; and
   a classifier fusion module implemented in hardware, the classifier fusion module coupled to receive the different classification outputs from each of the N-number of two-state classifiers and configured, upon receipt thereof, to classify the user state as one of up to $2^N$ different classification states using a predetermined combinational construct.

7. The system of claim 6, wherein the predetermined combinational construct comprises a multi-dimensional table.

8. The system of claim 6, wherein each of the different general states are functionally related.

9. A method for classifying a user state, comprising the steps of:
   sensing a first general state of a user;
   sensing a second general state of a user;
   using a first two-state classifier to classifying the first general state of the user as either a first state or a second state to determine a first user classification;

using a second two-state classifier to classify the second general state of the user as either a third state or a fourth state to determine a second user classification; and classifying the user state as one of at least three different classification states based on the first user classification and the second user classification using a predetermined multi-dimensional combinational construct.

10. The method of claim 9, wherein the predetermined combinational construct comprises a multi-dimensional table.

11. The method of claim 9, wherein the first general state and the second general state are functionally related.

12. The method of claim 9, further comprising:

sensing a third general state of the user; and using a third two-state classifier to classify the third general state of the user as either a fifth state or a sixth state to determine a third user classification; and classifying the user state as one of up to eight different classification states, based on the first, second, and third user classifications.

13. The method of claim 9, further comprising:

sensing (N−2) additional and different general states of the user;

using (N−2) additional two-state classifiers to classify each of the different general states of the user as one of two states, to thereby determine a total of N-number of user classifications; and classifying the user state as one of up to $2^N$ different classification states, based on the N-number of user classifications.

* * * * *